United States Patent [19]

Marocco et al.

[11] 4,142,628
[45] Mar. 6, 1979

[54] DIRECT DISPENSING SUTURE PACKAGE FOR A MULTIPLE OF STERILE SURGICAL SUTURES WITH OR WITHOUT NEEDLES ATTACHED

[75] Inventors: Frank J. Marocco, Eastchester, N.Y.; Lelia A. Bolanowski, Bethel, Conn.

[73] Assignee: American Cyanamid Company, Stamford, Conn.

[21] Appl. No.: 797,216

[22] Filed: May 16, 1977

[51] Int. Cl.² ............................................. A61L 17/02
[52] U.S. Cl. .................................. 206/63.3; 206/388; 206/476
[58] Field of Search ................ 206/49, 63.3, 227, 363, 206/388, 408, 472, 476, 486, 491–492, 495; 128/335.5

[56] References Cited

U.S. PATENT DOCUMENTS

| | | | |
|---|---|---|---|
| 3,357,550 | 12/1967 | Holmes et al. | 206/63.3 |
| 3,869,044 | 3/1975 | Olsson et al. | 206/63.3 |
| 3,876,068 | 4/1975 | Sonnino | 206/63.3 X |
| 3,939,969 | 2/1976 | Miller et al. | 206/63.3 |
| 4,063,638 | 12/1977 | Marwood | 206/63.3 |
| 4,089,409 | 5/1978 | Cerwin | 206/63.3 |

*Primary Examiner*—Steven E. Lipman
*Attorney, Agent, or Firm*—Charles F. Costello, Jr.

[57] ABSTRACT

A surgical suture retaining label for needled and for non-needled multiple sutures is disclosed which permits direct dispensing of the suture. An envelope having a tearing notch and a tear angle guideline across the face of the envelope is also disclosed. When the envelope is torn from the tear notch along the guideline, the label is exposed. The needled and non-needled sutures are held together by a tab. When the tab is pulled, the multiple sutures are directly dispensed from the label.

10 Claims, 9 Drawing Figures

DIRECT DISPENSING SUTURE PACKAGE FOR A MULTIPLE OF STERILE SURGICAL SUTURES WITH OR WITHOUT NEEDLES ATTACHED

BACKGROUND OF THE INVENTION

This invention relates to a suture label which permits direct dispensing of a multiple of sterile surgical sutures with or without needles attached and to a tearable suture envelope that can be torn from a tear notch across the face of the envelope so as to expose the label. A suture is a strand of material suitable for suturing, with or without an attached needle or needles, used for ligating or other surgical procedures.

The packaging of many commercial products is essential to the proper end use of the product and thus forms an integral part of the overall product design. The significance of packaging is most evident in the packaging or surgical sutures. It is essential that the package protect the product and maintain sterility throughout its period of potential use. Sutures may be stored in hospitals for several years, although the usual storage time is much shorter. It is essential that the package provide rapid and positive means of identification and release the product undamaged ready for use by the surgeon. There are many sizes of sutures, and many materials of construction such as catgut or polyglycolic acid for absorbables, silk, cotton, nylon, dacron, polyethylene, polypropylene, stainless steel, insulated stainless steel and other materials for use as non-absorbables. There are several different needle types in common use including pointed straight, pointed curved, three cornered straight, three cornered curved, curved both regular and reverse cutting, and needles with side cutting edges of various types. The variations and combinations of each of these to meet the preference of many surgeons for different operative procedures means that the suture manufacturer needs to supply different suture combinations running into the thousands. The importance of positive identification and efficient, economical packaging can thus be readily appreciated.

It is also important to provide convenience to the user and limit the risk of accidently enclosing foreign items in the patient by limiting the number of extraneous packaging materials associated with use of the product in the operating theater. A count is often kept to ensure that each item is accounted for and removed from the operating field. Considering the ramifications of enclosing such material in the patient accidently during surgical procedures, it is obviously essential to minimize this hazard.

It is also important that the surgical package properly present the sutures suitably oriented within the package so that the user can rapidly and reliably have access to the suture ends or needles in the proper position for dispensing from the package.

It is important also, to provide a standard packaging format for all multiple suture materials to limit confusion on the part of the user during surgical procedures. Over the years various package styles have evolved that have detracted from user convenience and operating room efficiency. For purposes of storage in the hospital as well as economy of manufacture, it is highly desirable that as many suture combinations as feasible be packaged in a minimum number of different package styles and shapes and storage units. It is quite common to package 3 dozen identical sutures in a box. It is convenient to have most of the boxes about the same size and shape, so that the hospital may store them most conveniently. It is also convenient from the manufacturers stand point to be able to reduce his inventory of box sizes and to be able to use the same components for the maximum number of suture combinations in the product line.

It is essential that a package containing multiple surgical sutures with needles protect the sutures from contact with the sharp point or cutting edge of the needles which could partially cut the suture or the package. Also the armed needle edges and point need to be protected so as to maintain their sharpness.

These requirements are so rigorous and of such importance that many different package designs have been tried. Generally, these designs disclose multiple surgical sutures packaged in a plastic or foil strippable envelope. Contained in the strippable envelope is an inner envelope or pouch, which is sterile. The suture strands have been formed into various configurations of coils and loops, contained in or on various retainers, labels, or reels, within the inner envelope. The multiple sutures are normally prepared for the surgeon by stripping the outer envelope and transferring the inner envelope by sterile forceps, or by projecting it across a sterile barrier, into the sterile areas of the operating room. The inner envelope is opened at the time of use.

The inner envelope and suture retaining label of the present invention for multiple needled and non-needled sutures have advantages over these designs. After tearing the inner envelope of the present invention, the suture retaining label is exposed. The label can then be used for direct dispensing of the multiple sutures without extracting it from the inner envelope. Access to the multiple sutures is provided from the label by a tab which is pulled after tearing the inner envelope.

Because the inner envelope and suture retaining label remain together after opening, the proliferation of packaging materials within the immediate area of the operation or other surgical procedure is reduced.

Still further, in most operations and surgical procedures, the materials used for the operation or surgical procedure are counted subsequent to the operation or surgical procedure. The label and inner envelope of the present invention provide a readily identifiable and countable package. Finally, the size of the needle and the type of suture strand can be printed on the inner envelope and on the tab. This provides ready identification in a surgical procedure where more than one size and type of suture is used. The possibility of a mix-up in the sizes and types is also reduced because the suture is directly dispensed from the label contained in the inner envelope.

SUMMARY OF THE INVENTION

The direct dispensing multiple needled surgical sutures label comprises four panels. This label and the multiple non-needled surgical sutures label can also be termed the suture retaining label.

The four panel multiple needled surgical sutures label comprises a back panel. Attached to one side of the back panel by tandem score lines is a strand cover flap. A notch is located on the top portion of the strand cover flap. The notch is also adjacent to the back panel.

Attached to the bottom of the back panel by tandem score lines is a label cover flap. The label cover flap contains a diagonal cut which connects the bottom of the label flap with one side of the label flap. Attached to the label cover flap on the side opposite from the diagonal cut is a side flap. The side flap is also attached by tandem score lines.

The suture retaining label is loaded by folding the strand cover flap over the back panel along the tandem score lines. Multiple needled surgical suture strands held together by a tab are then loaded between the panel and the strand cover flap. The tab and the needled end of the surgical suture strands are placed over the notch. The label cover flap is then folded over the strand cover flap and the side flap is folded under the back panel. When the tab is lifted, the multiple needled surgical sutures are directly dispensed from the suture retaining label.

The direct dispensing multiple needled surgical sutures retaining label described above can be manufactured from stiff sterilizable stock.

In another preferred embodiment, a suture package consisting of a sealed envelope having a tearing notch and a tear angle guideline encloses the suture retaining label described above. The suture retaining label is inserted into the suture package so that the notch is adjacent to the tear angle guideline of the sealed envelope. Thus when the envelope is opened from the tearing notch along the tear angle guideline, the tab holding together the multiple needled surgical sutures is exposed.

In yet another preferred embodiment, a double envelope suture package is within the scope of this invention. In this embodiment, the sealed envelope enclosing the suture retaining label would be contained in a strippable outer envelope.

The direct dispensing multiple non-needled surgical sutures retaining label comprises three panels. An upper strand cover flap and a lower strand cover flap are attached to a front panel by tandem score lines. A notch is located on the top portion of the front panel adjacent to the upper strand cover flap. In the preferred embodiment, this notch is V-shaped. The sutures retaining label is loaded by placing multiple non-needled surgical suture strands held together by a tab on the underside of the front panel. The tab and the ends of the surgical suture strands are then placed over the notch. The strand cover flaps are then folded under the front panel. When the tab is lifted, the multiple non-needled surgical sutures are directly dispensed from the label.

In the preferred embodiment, the suture retaining label is manufactured from stiff sterilizable stock.

In another preferred embodiment, the lower strand cover flap is shorter than the upper strand cover flap. When the multiple non-needled surgical suture strands are loaded onto the front panel, the lower strand cover flap is folded under the front panel and the upper strand cover flap is folded over the lower strand cover flap.

In yet another preferred embodiment, the upper strand cover flap can have locking slits on the top portion and the lower strand cover flap can have locking slits on the bottom portion. When the multiple non-needled surgical suture strands held together by a tab are placed on the front panel and the tab and the ends of the surgical suture strands are placed over the notch, the strand cover flaps are folded under the front panel. In this position the strand cover flaps are held together by the locking slits.

A suture package consisting of a sealed envelope having a tearing notch and a tear angle guideline is within the scope of this invention. In this embodiment, the direct dispensing multiple non-needled surgical sutures retaining label is enclosed within the envelope. The notch of the suture retaining label is adjacent to the tear angle guideline of the envelope. When the envelope is opened, the tab holding together the multiple non-needled surgical suture strand is exposed.

A double envelope suture package is also within the scope of this invention. The double envelope comprises a strippable outer envelope containing a sealed envelope as described in the above paragraph. Enclosed within the sealed envelope is a multiple non-needled surgical sutures retaining label. The notch of the suture retaining label is adjacent to the tear angle guideline of the sealed envelope.

DESCRIPTION OF THE INVENTION

The present suture label is, and remains, as a single piece within the inner envelope. In the preferred embodiment, the inner envelope which encloses and protects the suture in its label is notched and fits around the label so that it may be breached starting at the notch and torn open at the appropriate angle indicated, without tearing the envelope into more than one piece. The label is exposed during the tearing operation. Access to the multiple sutures is provided from the label by a tab. The tab also holds together the multiple sutures. The tab is grasped with the hand or with forceps and pulled gently and evenly, dispensing the multiple sutures. The present invention, and its advantages are also apparent from detailed descriptions of certain embodiments thereof which follow.

The four panel label for the multiple needled sutures is designed to protect the strand and envelope from damage by the needles. A U-shaped notch is specifically located between the back panel and the strand cover flap. The size and configuration of the notch assists to hold the needles and the tab in proper orientation, and to aid the grasping of the tab and the dispensing of the multiple needled sutures with needle holders or by hand. The three panel label for the multiple non-needled sutures has a V-shaped notch located between the back panel and one of the side flaps. The V-shaped notch serves a similar purpose for dispensing multiple non-needled sutures as does the U-shaped notch for multiple needled sutures.

Both labels are preferably of a sterilizable paper, of about 90 lb. weight, capable of withstanding alcoholic solutions, heat, steam, gas, or radiation sterilization without adverse effects.

Figure 9:
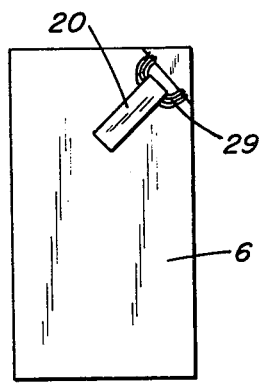
FIG. 9 shows the positioning of the label of FIG. 8 with multiple non-needled sutures for insertion into the inner envelope.

An important aspect of the present invention is having a tearable foil envelope that can be torn from a tear notch across the face so as to expose the suture retaining label, with part of the label being exposed to permit direct dispensing of the multiple sutures -- that is, the multiple sutures, with or without needles attached can be pulled out of the suture retaining label while the label remains in the envelope. Note the tear notch is at such a location that the label is retained in the foil envelope by an untorn corner. This avoids clutter in the operating room, as the entire label and package assembly, though torn, is in a single piece. FIG. 9 of U.S. Pat. No. 3,876,068 teaches a tear notch for a surgical suture package. This patent is incorporated herein by reference.

When the multiple sutures contain needles, the inner envelope and the sutures are both protected from the armed edges of the needles by the needle protection flap and the strand cover flap, respectively.

Figure 7:
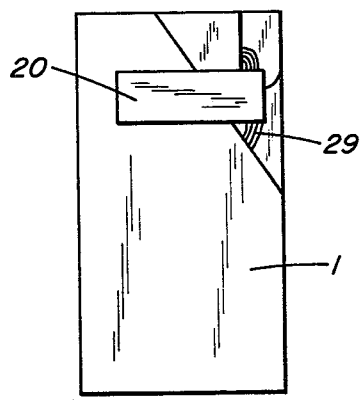
FIG. 7 shows the positioning of the label and tab of FIG. 6 for insertion into the inner envelope.

A prepared multiple needled sutures label is shown in FIG. 7. The suture is enclosed and sealed in a notched 21 inner envelope 25 which is shown in FIG. 2. The inner envelope in turn is sealed in a strippable outer envelope 31 shown in FIG. 1.

The inner envelope may conveniently be made of a moisture proof material such as a 25 lb., calendered, bleached, pouch paper laminated with about a ½ mil of polyethylene to a metallic foil such as about a 1 mil aluminum foil which is again laminated to 1 mil polyethylene as an inner sealable layer. Such a material is disclosed in U.S. Pat. No. 3,728,839, incorporated herein by reference. Such material is essentially moisture proof so that synthetic absorbable sutures such as those of polyglycolic acid are protected from hydrolitic degradation. A similar material, eg., Surlyn ® manufactured by E. I. Du Pont Co., Wilmington, Delaware, may be used for the packaging of catgut sutures which are packaged with a desired quantity of alcohol solution to maintain plasticity. Some sutures in which the moisture content is immaterial may also be packaged in the same material to maintain consistency of use and packaging standards.

Figure 1:
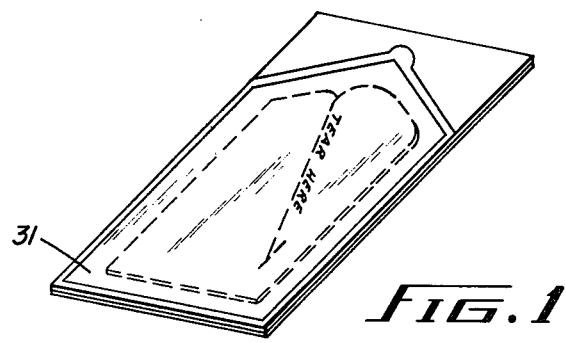
FIG. 1 shows a strippable outer envelope containing a tearable foil inner envelope.
Figure 2:
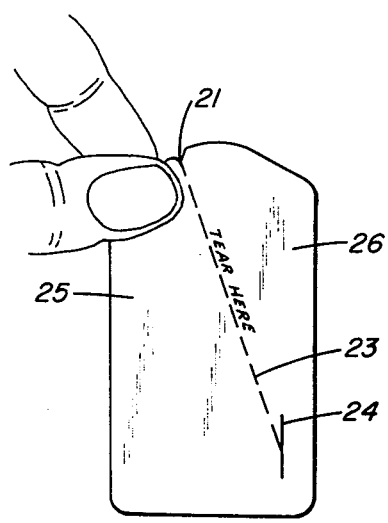
FIG. 2 shows the tearable inner envelope in position for use.
Figure 3:
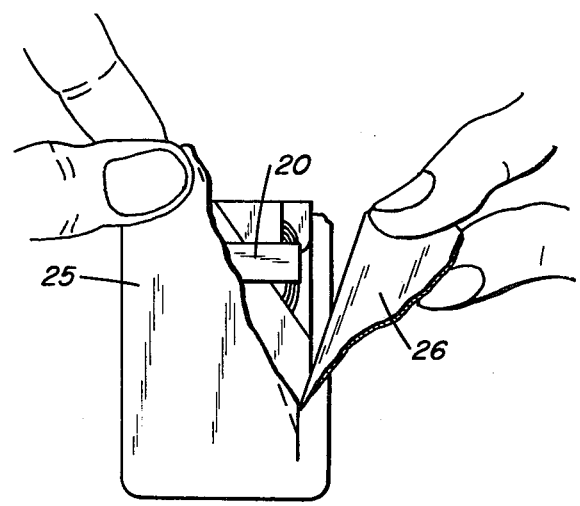
FIG. 3 shows the inner envelope being torn exposing the label and the tab for multiple needled sutures.

Referring to FIG. 1 and 2, the outer envelope 31 is peeled off. Using the tearing notch 21 as a start the user may then open the inner envelope 25 by tearing the laminate longitudinally along the dotted guideline 23 to stop line 24 without detaching the torn portion 26. This action exposes the label as shown in FIG. 3. To aid the user in proper use of the package a tear arrow could be indicated on the dotted guideline 23.

FIG. 3 shows the availability of the tab 20 after the inner envelope 25 has been torn. The torn portion 26 is not detached from the inner envelope.

Figure 4:
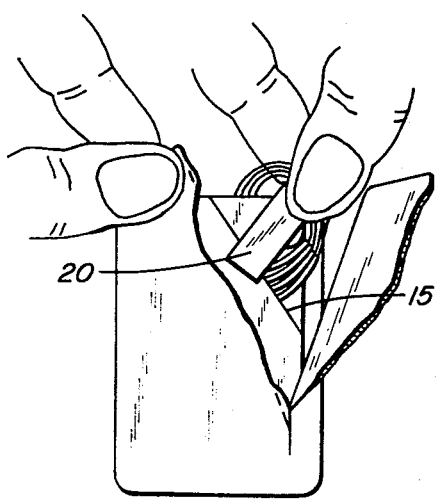
FIG. 4 describes one embodiment of the use of the direct dispensing package by removing the tab with the thumb and index finger.

FIG. 4 shows the tab 20 being grasped by the thumb and index finger of the user. FIG. 4 also shows part of the label cover flap 1 with a diagonal cut 15 under and adjacent to tab 20. The diagonal cut 15 in label flap 1 assists in allowing access to the tab.

Figure 5:
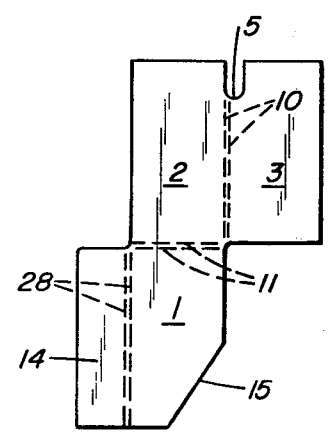
FIG. 5 is a front view of the multiple needled sutures label.

FIG. 5 is a front view of the multiple needled sutures label. The label is cutout and scored from a sheet of sterilizable paper.

As shown in FIG. 5, the sutures label consists of a back panel 2 to which is attached respectively, by tandem score lines 10, 11, a strand cover flap 3 and a label cover flap 1. Side flap 14 is attached by tandem score lines 28 to label cover flap 1. Back panel 2 is partially separated from strand cover flap 3 by notch 5. Notch 5 is U-shaped. Diagonal cut 15 on label cover flap 1 allows access to the multiple needled sutures tab when the label is contained in the inner envelope. The tab of the multiple needled sutures is over and adjacent the diagonal cut 15 for direct dispensing by hand or by forceps of the multiple needled sutures.

Figure 6:
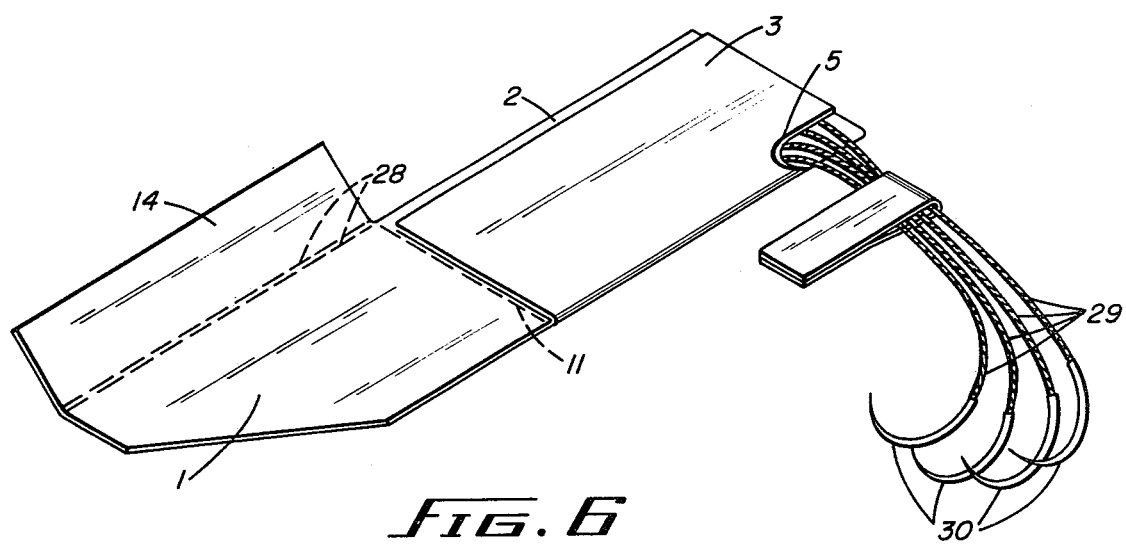
FIG. 6 shows the insertion of the multiple needled suture strands into the label of FIG. 5.

FIG. 6 shows the preferred folding of the strand cover flap 3 over the back panel 2 along tandem score lines 10. The needled ends of the suture strands 29 is also shown in the appropriate position after inserting the multiple needled suture strands into the label. The configuration of the multiple strands in the label can be any one or a series of loops or coils that allow the multiple strands to be directly dispensed without tangling. The needled end of the suture strands 29 and the multiple needles 30, held by notch 5, are then placed on top of the strand cover flap 3. The label cover flap 1 is then folded along tandem score lines 11. Finally, side flap 14 is folded along tandem score lines 28 behind back panel 2.

FIG. 7 shows the proper positioning of the needled ends of the suture strands 29 and the tab 20 in the multiple needled sutures label. The relationship of the tab 20 to the label cover flap 1 is important to the direct dispensing of the multiple needled sutures. That is, in the preferred embodiment, tab 20 is not contained in label cover flap 1.

FIG. 7 also shows the label cover flap 1 folded over the multiple needles thus protecting the inner envelope from damage by the butts of the needles. With the side flap 14, the label cover flap 1 is also an aid in keeping the needles properly oriented in the label during processing or transit.

Figure 8:
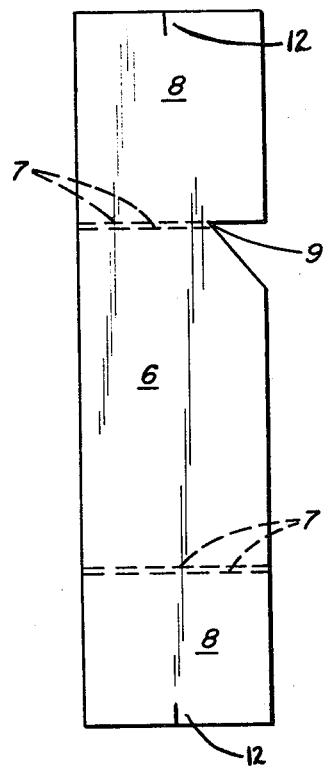
FIG. 8 is a front view of the multiple non-needled sutures label.

FIG. 8 is a front view of the multiple non-needled sutures label. The label is cut out and scored from a sheet of sterilization paper. As shown in FIG. 8, the sutures label consists of a front panel 6 to which is attached, at the top and bottom by tandem score lines 7, strand cover side flaps 8. The top strand cover side flap 8 is partially separated from front panel 6 by notch 9. Notch 9 is V-shaped. The tab of the multiple non-needled sutures is over and adjacent the notch 9 for direct dispensing by hand or by forceps of the multiple non-needled sutures.

The multiple non-needled sutures are inserted into the label from the rear. That is, the rear of front panel 6 in FIG. 8. The tab holding the non-needled suture strands is then laid over notch 9. The configuration of the multiple strands in the label can be any one or a series of loops, coils, serpentine or helix configurations that allow the multiple strands to be directly dispensed from the label without tangling. The side flaps 8 are then folded along tandem score lines 7. In the preferred embodiment, the top strand cover side flap is slightly larger than and folded over the bottom strand cover side flap for inserting into the bottom of the inner envelope. In yet another preferred embodiment, the upper strand cover side flap 8 can have locking slits 12 on the top portion and the lower strand cover side flap 8 can have locking slits on the bottom portion. When the multiple non-needled surgical suture strands held together by a tab are placed on the front panel 6 and the tab and the ends of the surgical suture strands are placed over the notch 9, the strand cover side flaps are folded along the tandem score lines 7 under the front panel. In this position the strand cover side flaps 8 are held together by the locking slits 12.

FIG. 9 shows the proper positioning of the ends of the suture strands 29 and the tab 20 in the multiple non-needled sutures label. The relationship of the tab 20 to the front panel 6 is important. That is, in the preferred embodiment, tab 20 is not contained in front panel 6.

We claim:

1. A direct dispensing multiple needled surgical suture retaining label comprising
   a back panel;
   a strand cover flap adjacent one side of said panel containing tandem score lines;
   a notch on the top portion of said strand flap and adjacent said panel;
   a label cover flap adjacent the bottom of said panel containing tandem score lines;
   a diagonal cut connecting the bottom and a side portion of said label flap;
   a side flap adjacent and connected to said label flap, and opposite said cut, containing tandem score lines;
   whereby said strand flap is folded on said tandem score lines onto said panel, multiple needled surgical suture strands held together by a tab are contained between said panel and said strand flap with the tab and the needled ends of said surgical suture strands placed onto said notch, and said label flap is folded on said tandem score lines onto said strand flap and said said flap is folded on said tandem score lines under said panel such that when said tab is lifted, the multiple needled surgical sutures are directly dispensed from said label.

2. A direct dispensing surgical suture retaining label described in claim 1 manufactured from stiff sterilizable stock.

3. A suture package consisting of a sealed envelope having a tearing notch and a tear angle guideline enclosing a lable and multiple needled surgical suture strands, the improvement wherein said lable is a direct dispensing surgical suture retaining label as set forth in claim 1 in which the notch of said label is adjacent to the tear angle guideline of said envelope, such that when said envelope is opened, the tab of said multiple needled surgical sutures is exposed.

4. A double envelope suture package comprising a strippable outer envelope containing a sealed envelope described in claim 3.

5. A direct dispensing multiple non-needled surgical suture retaining label comprising
   a front panel;
   an upper strand cover flap adjacent said panel containing tandem score lines;
   a notch on the top portion of said panel and adjacent said upper flap;
   a lower strand cover flap adjacent said panel; and opposite said upper flap, containing tandem score lines;
   whereby multiple non-needled surgical suture strands held together by a tab are placed on said panel with the tab and the ends of said surgical suture strands placed over said notch, and said flaps are folded on said tandem score lines enclosing said surgical suture strands such that when said tab is lifted, the multiple non-needled surgical sutures are directly dispensed from said label.

6. A direct dispensing surgical suture label described in claim 5 manufactured from stiff sterilizable stock.

7. A direct dispensing multiple non-needled surgical sutures label described in claim 5 wherein the lower strand cover flap is shorter than the upper strand cover flap, said lower flap is folded on said tandem score lines under said front panel and said upper flap is folded on said tandem score lines over said lower flap.

8. A direct dispensing multiple non-needled surgical sutures label described in claim 5 having locking slits on the top portion of said upper flap and on the bottom portion of said lower flap.

9. A suture package consisting of a sealed envelope having a tearing notch and a tear angle guideline enclosing a label and multiple non-needled surgical suture strands, the improvement wherein said lable is a direct dispensing surgical sutures label as set forth in claim 5 in which the notch of said label is adjacent to the tear angle guideline of said envelope, such that when said envelope is opened, the tab of said multiple non-needled surgical sutures is exposed.

10. A double envelope suture package comprising a strippable outer envelope containing a sealed envelope described in claim 9.

* * * * *